United States Patent
Chen et al.

(10) Patent No.: US 10,139,259 B2
(45) Date of Patent: *Nov. 27, 2018

(54) SYSTEM AND METHOD FOR METERING GAS BASED ON AMPLITUDE AND/OR TEMPORAL CHARACTERISTICS OF AN ELECTRICAL SIGNAL

(71) Applicant: General Electric Company, Schenectady, NY (US)

(72) Inventors: Nannan Chen, Clifton Park, NY (US); Ertugrul Berkcan, Clifton Park, NY (US); Mengli Wang, Niskayuna, NY (US); Roman Leon Artiuch, Houston, TX (US)

(73) Assignee: General Electric Company, Schenectady, NY (US)

( * ) Notice: Subject to any disclaimer, the term of this patent is extended or adjusted under 35 U.S.C. 154(b) by 108 days.

This patent is subject to a terminal disclaimer.

(21) Appl. No.: 15/332,757

(22) Filed: Oct. 24, 2016

(65) Prior Publication Data
US 2017/0038237 A1 Feb. 9, 2017

Related U.S. Application Data

(63) Continuation-in-part of application No. 14/561,431, filed on Dec. 5, 2014, now abandoned.

(51) Int. Cl.
*G01F 5/00* (2006.01)
*G01F 25/00* (2006.01)
(Continued)

(52) U.S. Cl.
CPC ............... *G01F 5/00* (2013.01); *E21B 43/34* (2013.01); *F17D 1/00* (2013.01); *G01F 25/0007* (2013.01); *G01N 33/0062* (2013.01)

(58) Field of Classification Search
CPC ........................................................ G01F 1/00
See application file for complete search history.

(56) References Cited

U.S. PATENT DOCUMENTS 3,559,482 A * 2/1971 Baker ................... G01F 1/6847
73/202
3,633,416 A 1/1972 Van Dyke et al.
(Continued)

FOREIGN PATENT DOCUMENTS

| CN | 201498051 U | 6/2010 |
|---|---|---|
| CN | 203719723 U | 7/2014 |
| CN | 204314987 U | 5/2015 |

OTHER PUBLICATIONS

Q A Stewart, "Regulation for new technology in gas metering", Ninth International Conference on Metering and Tariffs for Energy Supply, pp. 1-3, 1999, Birmingham, UK.
(Continued)

*Primary Examiner* — Harshad R Patel
(74) *Attorney, Agent, or Firm* — GE Global Patent Operation; Pabitra Chakrabarti

(57) ABSTRACT

A system for metering gas a fluid stream includes a primary conduit and a secondary conduit coupled to the primary conduit such that the secondary conduit receives a portion of a fluid stream passing through the primary conduit. A flow manager disposed in the primary conduit is configured to maintain a predetermined relationship between at least one first physical characteristic of the fluid stream and at least one second physical characteristic of the portion of the fluid stream. A sensor measures a flow characteristic of the portion of the fluid stream and a processor determines a flow parameter of the fluid stream based, at least in part, on the predetermined relationship and one of an amplitude or temporal characteristic of the electrical signal.

24 Claims, 8 Drawing Sheets

(51) Int. Cl.
  *G01N 33/00* (2006.01)
  *E21B 43/34* (2006.01)
  *F17D 1/00* (2006.01)

(56) References Cited

U.S. PATENT DOCUMENTS

| | | | | |
|---|---|---|---|---|
| 3,851,526 | A * | 12/1974 | Drexel | G01F 1/42 138/42 |
| 4,290,298 | A | 9/1981 | Severson | |
| RE31,570 | E * | 5/1984 | Drexel | G01F 1/42 138/42 |
| 4,475,387 | A * | 10/1984 | Hawk | G01F 1/6847 73/202.5 |
| 4,672,997 | A * | 6/1987 | Landis | G01F 1/6847 137/554 |
| 4,938,053 | A | 7/1990 | Jepson et al. | |
| 5,398,548 | A | 3/1995 | Ono | |
| 5,804,717 | A * | 9/1998 | Lucas | G01F 1/684 73/202 |
| 6,655,207 | B1 * | 12/2003 | Speldrich | G01F 1/40 73/202.5 |
| 6,681,623 | B2 * | 1/2004 | Bonne | G01F 1/40 73/202 |
| 6,843,122 | B2 * | 1/2005 | Kim | G01F 1/6847 702/45 |
| 7,651,263 | B2 * | 1/2010 | Zolock | G01F 1/6847 374/1 |
| 7,905,139 | B2 * | 3/2011 | Lull | G01F 1/6847 73/202.5 |
| 8,356,623 | B2 * | 1/2013 | Isobe | G01F 1/6842 137/486 |
| 8,418,549 | B2 * | 4/2013 | Speldrich | G01F 5/00 73/202.5 |
| 8,499,786 | B2 * | 8/2013 | Zolock | G05D 7/0635 137/487 |
| 8,966,970 | B2 | 3/2015 | Berkcan et al. | |
| 9,032,790 | B2 | 5/2015 | Braun et al. | |
| 2003/0115950 | A1 * | 6/2003 | Ambrosina | G01F 1/684 73/202.5 |
| 2003/0115951 | A1 * | 6/2003 | Ambrosina | G01F 1/684 73/202.5 |
| 2006/0101907 | A1 * | 5/2006 | Shajii | G01F 1/6847 73/202.5 |
| 2006/0101908 | A1 * | 5/2006 | Meneghini | G01F 1/6847 73/202.5 |
| 2007/0113641 | A1 * | 5/2007 | Ding | G01F 1/6847 73/202.5 |
| 2007/0125168 | A1 * | 6/2007 | Kouno | G01F 1/684 73/204.16 |
| 2007/0151335 | A1 * | 7/2007 | Sparks | G01F 1/8445 73/204.26 |
| 2008/0053204 | A1 * | 3/2008 | Neville | G01N 27/403 73/61.71 |
| 2009/0007654 | A1 * | 1/2009 | Niikawa | G01F 1/00 73/202 |
| 2009/0095068 | A1 * | 4/2009 | Redemann | G01F 1/6847 73/202 |
| 2010/0030388 | A1 * | 2/2010 | Wang | G01F 1/363 700/282 |
| 2014/0165718 | A1 * | 6/2014 | Berkcan | G01F 1/6842 73/204.21 |
| 2016/0161307 | A1 * | 6/2016 | Berkcan | G01N 33/0062 73/861.08 |
| 2017/0074704 | A1 * | 3/2017 | Berkcan | G01N 33/0062 |
| 2018/0143055 | A1 * | 5/2018 | Artiuch | G01N 33/0006 |

OTHER PUBLICATIONS

Hayashi et al., "Evolution of next-generation gas metering system in Japan", 2014 IEEE MTT-S International Microwave Symposium (IMS2014), pp. 1-4, Jun. 1-6, 2014, Tampa, FL.

Extended European Search Report and Opinion issued in connection with corresponding EP Application No. 17197268.0 dated Mar. 22, 2018.

* cited by examiner

SYSTEM AND METHOD FOR METERING GAS BASED ON AMPLITUDE AND/OR TEMPORAL CHARACTERISTICS OF AN ELECTRICAL SIGNAL

CROSS REFERENCE TO RELATED APPLICATIONS

This application is a continuation-in-part of U.S. Nonprovisional patent application Ser. No. 14/561,431, filed on Dec. 5, 2014, entitled "SYSTEM AND METHOD FOR METERING GAS BASED ON AMPLITUDE AND/OR TEMPORAL CHARACTERISTICS OF AN ELECTRICAL SIGNAL," (originally titled "SYSTEM AND METHOD FOR METERING GAS"), which is incorporated by reference in its entirety.

BACKGROUND

The field of the disclosure relates generally to fluid delivery systems and, more specifically, to fluid metering systems and methods of metering fluids in such systems.

Currently, metering of fluids entails use of various types of flow sensing devices such as mass flow sensing devices to measure a mass flow rate of the fluid. Some flow sensors determine the mass flow rate of the gas based on an amplitude measurement. Other flow sensing devices involve vortex-based sensing where, for example, a frequency at which vortices are formed is essentially proportional to the flow rate of the fluid. Consequently, the volumetric flow rate is determined based on the frequency at which the vortices are formed.

Generally, currently available fluid metering systems offer the advantage of high sensitivity in a low flow range. However such fluid metering systems are typically adversely impacted by gas density fluctuations, moisture fluctuations, gas mixture fluctuations, and the like. Consequently, such fluid metering systems fail to provide a direct and accurate volumetric flow rate measurement. For example, the density of the fluid may vary depending on factors such as pressure, temperature, and composition of the fluid. These factors adversely affect the quality and accuracy of flow measurement. On the contrary, vortex-based sensing devices entail direct volumetric flow rate measurement. However, measurement of the flow rate using the vortex-based sensing devices is adversely impacted when a velocity of the fluid is low as the low velocity of the fluid affects formation of vortices.

BRIEF DESCRIPTION

In one aspect, a system for metering a fluid stream is provided. The system includes a primary conduit and a secondary conduit in fluid communication with primary conduit. The secondary conduit is configured to receive a portion of a fluid stream passing through the primary conduit. A flow manager disposed in the primary conduit is configured to maintain a predetermined relationship between at least one first physical characteristic of the fluid stream and at least one second physical characteristic of the portion of the fluid stream. The metering system further includes a sensor configured to generate an electrical signal in response to a flow characteristic of the portion of the fluid stream in the secondary conduit. A processor communicatively coupled to the sensor determines a flow parameter of the fluid stream based, at least in part, on the predetermined relationship between the first physical characteristic and the second physical characteristic, and at least one of an amplitude characteristic of the electrical signal and a temporal characteristic of the electrical signal.

In another aspect, a metering assembly for use in a fluid meter having a primary conduit is provided. The metering assembly includes a secondary conduit configured to be coupled to the primary conduit and, when coupled to the primary conduit, to receive a portion of a fluid stream passing through the primary conduit. A flow manager disposed in the primary conduit is configured to maintain a predetermined relationship between at least one first physical characteristic of the fluid stream and at least one second physical characteristic of the portion of the fluid stream. The metering system further includes a sensor configured to generate an electrical signal in response to a flow characteristic of the portion of the fluid stream in the secondary conduit. A processor communicatively coupled to the sensor determines a flow parameter of the fluid stream based, at least in part, on the predetermined relationship between the first physical characteristic and the second physical characteristic, and at least one of an amplitude characteristic of the electrical signal and a temporal characteristic of the electrical signal.

In yet another aspect, a method for metering a fluid stream within a primary conduit is provided. The method includes diverting a portion of the fluid stream into a secondary conduit, wherein diverting the portion of the fluid stream includes maintaining a predetermined relationship between at least one first physical characteristic of the fluid stream and at least one second physical characteristic of the portion of the fluid stream. The method further includes generating, by a sensor, an electrical signal corresponding to a flow characteristic of the portion of the fluid stream and calculating a flow parameter of the fluid stream. Calculation of the flow parameter of the fluid stream is based, at least in part, on the predetermined relationship between the at least one first physical characteristic of the fluid stream and the at least one second physical characteristic of the portion of the fluid stream, and at least one of an amplitude characteristic of the electrical signal and a temporal characteristic of the electrical signal. The flow parameter of the fluid stream is based on the amplitude characteristic when the portion of the fluid stream is in a first flow regime and on the temporal characteristic when the portion of the fluid stream is in a second flow regime.

DRAWINGS

These and other features, aspects, and advantages of the present specification will become better understood when the following detailed description is read with reference to the accompanying drawings in which like characters represent like parts throughout the drawings, wherein.

DETAILED DESCRIPTION

Figure 1:
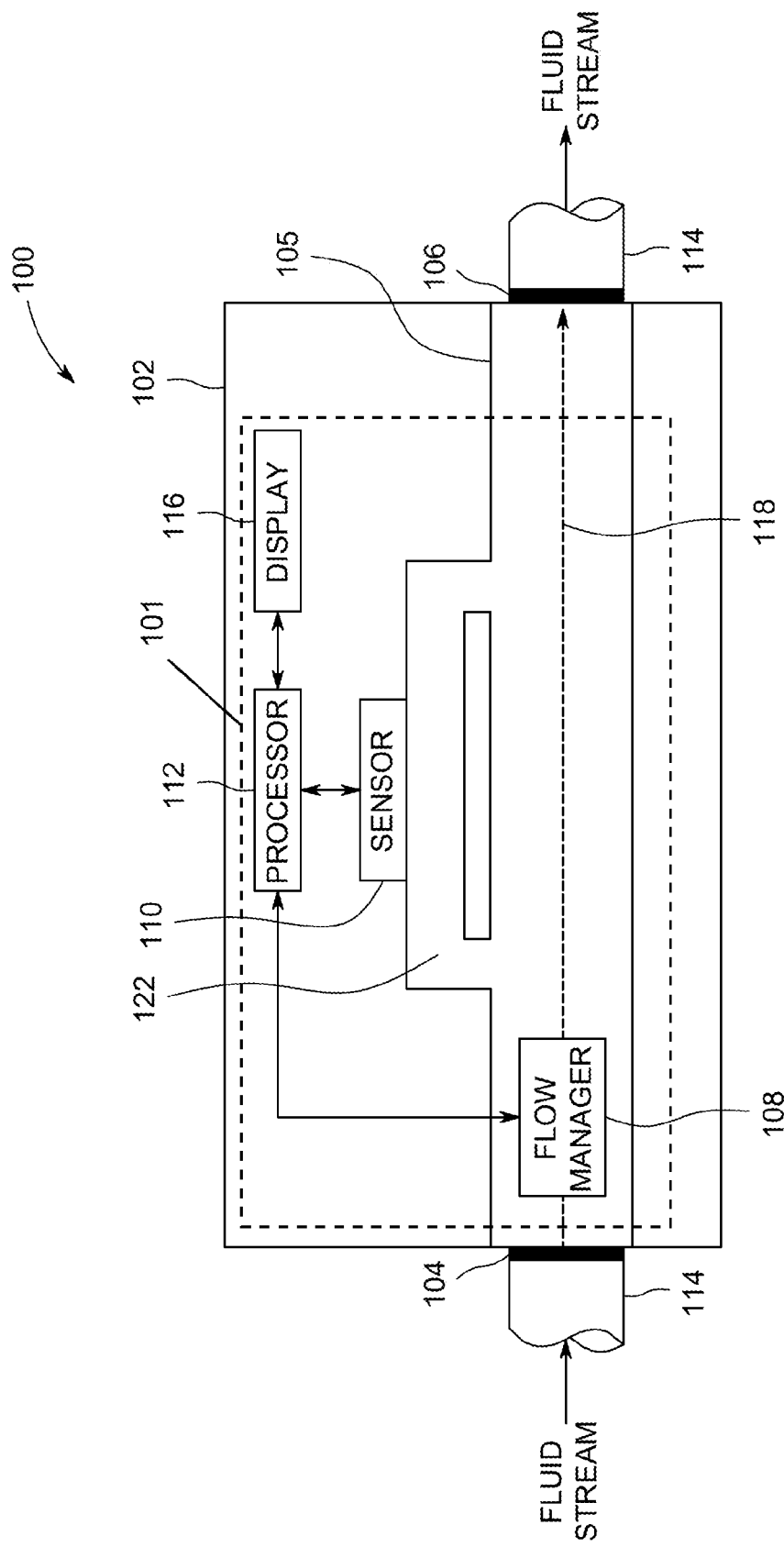
FIG. 1 is a schematic view of an exemplary metering system for metering a fluid stream.

The specification may be best understood with reference to the detailed figures and description set forth herein. Various embodiments are described hereinafter with reference to the figures. However, those skilled in the art will readily appreciate that the detailed description given herein with respect to these figures is for explanatory purposes as the method and the system extend beyond the described embodiments.

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

As used herein, the terms "processor" and "computer," and related terms, e.g., "processing device," "computing device," and "controller" are not limited to just those integrated circuits referred to in the art as a computer, but broadly refers to a microcontroller, a microcomputer, a programmable logic controller (PLC), and application specific integrated circuit, and other programmable circuits, and these terms are used interchangeably herein. In the embodiments described herein, memory may include, but it not limited to, a computer-readable medium, such as a random access memory (RAM), a computer-readable non-volatile medium, such as a flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program storage in memory for execution by personal computers, workstations, clients, and servers.

As used herein, the term "non-transitory computer-readable media" is intended to be representative of any tangible computer-based device implemented in any method of technology for short-term and long-term storage of information, such as, computer-readable instructions, data structures, program modules and sub-modules, or other data in any device. Therefore, the methods described herein may be encoded as executable instructions embodied in a tangible, non-transitory, computer-readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including without limitation, volatile and non-volatile media, and removable and non-removable media such as firmware, physical and virtual storage, CD-ROMS, DVDs, and any other digital source such as a network or the Internet, as well as yet to be developed digital means, with the sole exception being transitory, propagating signal.

The embodiments of fluid metering systems, as described herein, overcome a number of deficiencies of known fluid metering systems and provide an accurate and effective method for fluid metering over a wide range of operational conditions. Specifically, the embodiments described herein overcome the deficiencies and susceptibility to mismeasurement inherent in mass flow meters and vortex-based flow meters. More specifically, embodiments of fluid metering systems described herein include a primary conduit through which a stream of fluid passes and a secondary conduit coupled to the primary conduit that receives a portion of the fluid stream. A flow manager disposed in the primary conduit maintains a predetermined relationship between physical characteristics of the fluid stream in the primary conduit and the portion of the fluid stream in the secondary conduit. A sensor placed within the secondary conduit generates an electrical signal in response to a flow characteristic of the portion of the fluid stream and a processor determines a flow parameter of the fluid stream within the primary conduit based on the electrical signal and the predetermined relationship between the physical characteristics of the fluid stream and the portion of the fluid stream. More specifically, when the portion of the fluid stream is in a first flow regime, the processor determines the flow parameter based on an amplitude characteristic of the electrical signal. When the portion of the fluid stream is in a second flow regime, the processor determines the flow parameter based on a temporal characteristic of the electrical signal. In certain embodiments, the first flow regime corresponds to a substantially laminar flow regime and the second flow regime corresponds to a substantially turbulent flow regime. Embodiments of metering systems described herein are suitable for use across a wide range of applications as placement of the sensor in the secondary conduit facilitates use of a particular secondary conduit and sensor arrangement in a wide range of primary conduit sizes and configurations. Therefore, the embodiments described herein dynamically and adaptively meter fluids across a wide range of operational conditions, increasing the accuracy and reliability with which fluid metering may be conducted in a fluid distribution system.

FIG. 1 is a schematic view of an exemplary metering system 100 for metering a fluid stream. Metering system 100 includes a housing 102 having an input port 104 and an output port 106. In addition, metering system 100 includes a metering assembly 101 including a secondary conduit 122, a flow manager 108, a sensor 110, a processor 112, and a display 116. In metering system 100, processor 112 is disposed within or otherwise near housing 102. In alternative embodiments, processor 112 is remote from housing 102 but communicatively coupled to sensor 110 over a network including, without limitation, the Internet, a local area network (LAN), a wide area network (WAN), and a control system network such as a supervisory control and data acquisition (SCADA) network. Metering system 100 also includes an energy source, such as a battery (not shown), coupled to one or more of flow manager 108, sensor 110, and processor 112, in order to supply energy thereto.

Metering system 100 is operatively coupled to a pipeline 114 and configured to meter a fluid stream passing through pipeline 114. Pipeline 114 is generally part of a broader system for supplying a fluid to households, commercial facilities, and industrial facilities. For example, in certain embodiments, pipeline 114 is part of a gas supply system for supplying natural gas. Metering system 100 is operatively coupled to pipeline 114 such that a fluid stream, such as a gas stream, flowing through pipeline 114 is received at input port 104, passes through a primary conduit 105 disposed within housing 102, and is discharged from output port 106. Primary conduit 105 generally defines a flow passage 118 (shown in FIG. 1 as a dotted line) configured to facilitate passage of the fluid stream through housing 102, and more particularly, between input port 104 and output port 106. In certain embodiments, input port 104 and output port 106 are integrally formed as parts of housing 102. In other embodiments, input port 104 and output port 106 are operatively coupled to housing 102. As noted hereinabove, metering system 100 is configured to meter the fluid stream as it flows through primary conduit 105 between input port 104 and output port 106. The terms "meter" and "metering" as used herein, are used to refer to the determination of one or more flow parameters of the fluid stream flowing within primary conduit 105 including, without limitation, a mass flow rate, an accumulated volume of the fluid stream, a volumetric flow rate, a cumulative volume per a determined time unit, and any combination thereof.

Secondary conduit 122 in fluid communication with primary conduit 105. In metering system 100, secondary conduit 122 is shown as a bypass coupled to primary conduit 105. In other embodiments, secondary conduit 122 is otherwise in fluid communication with primary conduit 105. For example, in certain embodiments secondary conduit 122 is disposed within primary conduit 105. During operation, at least a portion of the fluid stream passing through primary conduit 105 enters secondary conduit 122. Flow manager 108 maintains a predetermined relationship between physical characteristics of the fluid stream in primary conduit 105 and the portion of the fluid stream in secondary conduit 122 such that the portion of the fluid stream in secondary conduit 122 may be correlated with the fluid stream in primary conduit 105. As the portion of the fluid stream passes through secondary conduit 122, sensor 110 generates an electrical signal in response to a flow characteristic of the portion of the fluid stream. As described below in more detail, processor 112 then determines a flow parameter of the fluid stream in primary conduit 105 based, at least in part, on the predetermined relationship maintained by flow manager 108 and the electrical signal generated by sensor 110.

In the exemplary embodiment, at least a portion of flow manager 108 is disposed within primary conduit 105 and is configured to maintain a predetermined relationship between physical characteristics of the fluid stream in primary conduit 105 and the portion of the fluid stream in secondary conduit 122. In certain embodiments, flow manager 108 is further configured to divert the portion of the fluid stream into secondary conduit 122. Flow manager 108 maintains a predetermined relationship that enables correlation of properties of the portion of the fluid stream in secondary conduit 122 with those of the fluid stream in primary conduit 105. Such relationships may include, without limitation, equating the physical characteristics or establishing a linear, exponential, logarithmic, or other defined relationship between the streams. Physical characteristics controlled or otherwise maintained by flow manager 108 include, without limitation, flow separability, pressure, temperature, mass flow rate, volumetric flow rate, and quantity of impurities. In certain embodiments, the predetermined relationship is based on the same physical characteristic for both the stream of fluid in primary conduit 105 and the portion of the stream in secondary conduit 122. For example, in such embodiments, the predetermined relationship correlates fluid pressures within the conduits. In other embodiments, the predetermined relationship is based on different physical characteristics in each conduit. For example, the predetermined relationship may correlate fluid pressure in first conduit 105 with fluid temperature in second conduit 122. Accordingly, flow manager 108 includes one or more active or passive devices configured to modify physical characteristics of one or both of the fluid stream in primary conduit 105 and the portion of the fluid stream in secondary. Examples of such devices include, without limitation, pressure control valves, flow control valves, shut-off valves, constrictions, expansions, flow diverters, heaters, coolers, obstructions, flow straighteners, filters, and fins. In certain embodiments, flow manager 108 includes an impurity segregator configured to remove impurities from the fluid stream using one or more segregation method including, without limitation, filtration, static force, magnetic force, and centrifugal force.

The term "separability," as used herein, refers to the tendency of a fluid stream to separate when in the vicinity of a surface, such as a surface of primary conduit 105. In fluid mechanics, a boundary layer is generally defined as a layer of a fluid stream in the vicinity of a bounding surface where the effect of the viscosity of the fluid stream is significant. Separation of the fluid stream occurs when the boundary layer travels against a sufficient pressure gradient that a speed of the boundary layer relative to the object (e.g., the surface of primary conduit 105) becomes substantially close to zero. Consequently, eddies, vortices, and similar disturbances form in the fluid stream. Separability of the fluid stream is often related to the lack of laminarity of the fluid stream. Accordingly, modifying a fluid stream to control separability generally includes modifying physical characteristics of the fluid stream to increase laminarity or turbulence of the fluid stream.

To calculate flow parameters of the fluid stream within primary conduit 105, processor 112 uses the predetermined relationship maintained by flow manager 108 and amplitude and/or temporal characteristics of the electrical signal generated by sensor 110. Examples of flow sensor 110 include, without limitation, a calorimetric flow sensor, a hot wire anemometer, a mass flow rate sensor, a volumetric flow rate sensor, a pressure sensor, a temperature sensor, or combinations thereof. Flow sensor 110 generally includes one or more sensing elements (not shown in FIG. 1), including, without limitation, micro-electromechanical flow sensing elements, thermopiles, temperature sensing elements, pressure sensing elements, and combinations thereof. For purposes of this disclosure, electrical signals generated by flow sensor 110 are generally considered to have amplitude and temporal characteristics. Amplitude characteristic include, without limitation, a magnitude, a scale, a breadth, and combinations thereof. Similarly, temporal characteristics include, without limitation, a period, a frequency, a zero crossing rate, a phase, a time-resolved demodulation, a frequency-resolved demodulation of the signal, and combinations thereof.

In metering system 100, processor 112 is operatively coupled to flow manager 108 and flow sensor 110. Processor 112 generally performs data processing and control functions of metering system 100. For example, in the exemplary embodiment, processor 112 receives and processes electronic signals generated by sensor 110. To the extent flow manager 108 includes one or more active devices, processor 112 is also configured to control, at least in part, functionality of at least a portion of the active devices of flow manager 108. In certain embodiments, processor 112 is communicatively coupled to at least one memory (not shown) configured to store data including, without limitation, executable instructions, control set points, data collected by processor 112, and diagnostic logs. For example, in certain embodiments, the at least one memory stores acceptable ranges of values of the one or more physical characteristics modified by flow modifier 108. In certain embodiments, processor 112 is configured to perform signal processing such as spectral analysis. Examples of techniques to facilitate signal processing that may be implemented by processor 112 include, without limitation, fast Fourier transform (FFT) algorithms, heterodyning, phase-locked looping, and combinations thereof.

In response to receiving an electrical signal from sensor 110, processor 112 determines at least one flow parameter of the fluid stream in primary conduit 105. More specifically, based on the flow characteristic of the portion of the fluid stream in secondary conduit 122 represented by the electrical signal generated by sensor 110 and the predetermined relationship between physical characteristics maintained by flow manager 108, processor 112 determines at least one flow parameter of the fluid stream within primary conduit 105. Processor 112 determines the flow parameter of the fluid stream within primary conduit 105 based on at least one of an amplitude characteristic and a temporal characteristic of the electrical signal and a geometric relationship between primary conduit 105 and at least one of secondary conduit 122 and sensor 110. In other embodiments, processor 112 determines the flow parameter of the fluid stream based on additional data including, without limitation, one or more geometrical relationships between primary conduit 105 and at least one of secondary conduit 122 and sensor 110. Examples of flow parameters include, without limitation, a mass flow rate of the fluid stream, an accumulated volume of the fluid stream, a volumetric flow rate of the fluid stream, a cumulative volume of the fluid stream per unit of time, and any combination thereof.

Metering system 100 includes display 116 which visualizes the values of the flow parameter determined by processor 112. Display 116 may include, without limitation, one or more of a light emitting diode (LED) display, a liquid crystal display (LCD), and a cathode ray tube (CRT) display. In metering system 100, display 116 is disposed on housing 102. In other embodiments, display 116 is disposed at a remote location. Display 116 is communicatively coupled to processor 112. In certain embodiments, display 116 is communicatively coupled to processor 112 via a wired medium over which communication is facilitated using a serial, parallel, or other communication protocol. In other embodiments, display 116 is coupled to processor 112 via a wireless communication link. In such embodiments, metering system 100 further includes a wireless communication unit (not shown) to facilitate data communication between processor 112 and display 116 over the wireless communication link. The wireless communication unit facilitates communication using one or more wireless communication protocol including, without limitation, Bluetooth, Wi-Fi, Wi-Max, and cellular communication protocols such as 2G, 3G, and 4G. In certain embodiments, processor 112 is communicatively coupled to multiple displays, each display being communicatively coupled to processor 112 by one of a wired and wireless communication link.

Figure 2:
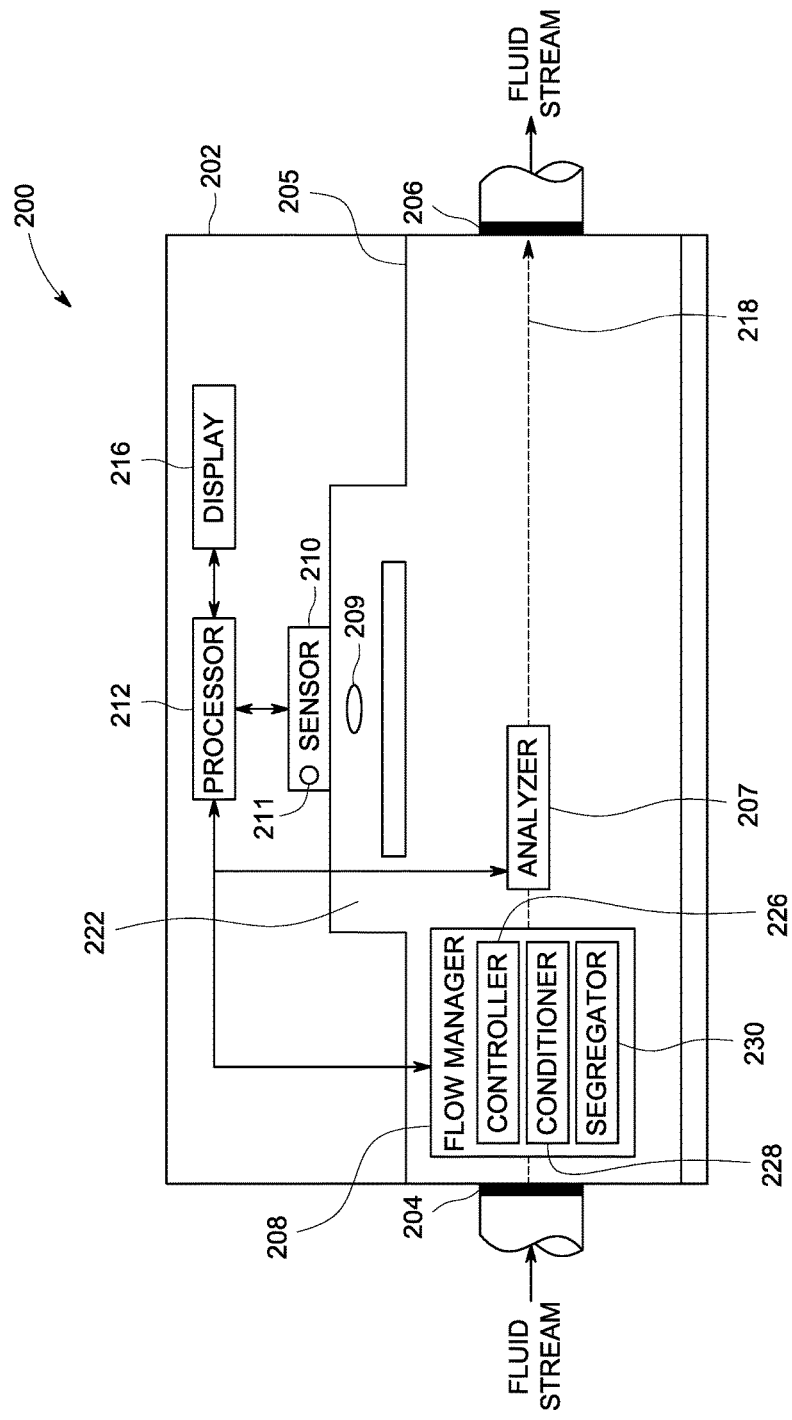
FIG. 2 is a schematic view of an alternative metering system for metering a fluid stream.

FIG. 2 is a schematic view of an alternative metering system 200 for metering a fluid stream. Metering system 200 includes a housing 202 having an input port 204 and an output port 206 and a primary conduit 205 extending therebetween. Primary conduit 205 defines a flow passage 218 that facilitates passage of a fluid stream between input port 204 and output port 206. Metering system 200 further includes a metering assembly 201 including a secondary conduit 222, a flow manager 208, an analyzer 207, a flow sensor 210, and a processor 212. Metering system 200 also includes a display 216, an energy source, such as a battery (not shown), and a wireless communication unit (not shown). The energy source generally supplies energy to at least one of flow manager 208, analyzer 207, flow sensor 210, and processor 212. The wireless communication unit is communicatively coupled to processor 212.

Flow manager 208 is configured to maintain a predetermined relationship between the fluid stream in primary conduit 205 and the portion of the fluid stream in secondary conduit 222. In metering system 200, flow manager 208 includes a flow controller 226, a flow conditioner 228, and an impurity segregator 230. Flow controller 226 includes a control valve (not shown) configured to selectively restrict the fluid stream from passing through primary conduit 205. In certain embodiments, flow controller 226 is configured to act as a shut-off valve, preventing the fluid stream from entering primary conduit 205. In other embodiments, flow controller 226 is configured to facilitate throttling of the fluid stream. Flow manager 208 also includes a flow conditioner 228 configured to control a separability of the flow of the fluid stream. The control of the separability of the fluid stream includes, without limitation, reducing at least one of turbulence, swirls, vortices, eddies, and asymmetric flow profiles in the fluid stream. Flow manager 208 further includes impurity segregator 230, which removes impurities from the fluid stream. Impurity segregator 230 may remove impurities using various methods including, without limitation, filtration, static force, magnetic force, and centrifugal force. Impurities removable by impurity segregator 230 include, without limitation, one or more of dust, foreign objects, glycol, hydrogen sulfide ($H_2S$), sulfur dioxide ($SO_2$), methyl mercaptan ($CH_4S$), carbonyl sulfide (COS), carbon disulfide ($CS_2$), nitrogen, carbon dioxide ($CO_2$), water vapor, and combinations thereof. Examples of devices and media for use as impurity segregator 230 include, without limitation, cyclone-type dust segregators, charcoal, activated carbon, monoethlamine (MEA) solution, iron filings, and the like.

Metering system 200 further includes an analyzer 207. Analyzer 207 is disposed at least partially within housing 202 such that analyzer 207 is aligned with one or more elements of flow manager 208. Analyzer 207 is configured to determine one or more non-flow rate characteristics of the fluid stream. The non-flow rate characteristics of the fluid stream may include, without limitation, density, mixture and composition, temperature, pressure, humidity, energy content, impurities levels, and any combination thereof. To facilitate determination of the non-flow characteristics, analyzer 207 includes one or more sensors configured to measure the non-flow characteristic of interest. In metering system 200, analyzer 207 is communicatively coupled to processor 212 and is configured to communicate the determined values of the non-flow rate characteristics to processor 212.

Metering system 200 includes a secondary conduit 222 in fluid communication with primary conduit 205. During operation, at least a portion of the fluid stream passing through primary conduit 205 also passes through secondary conduit 222. In certain embodiments, flow manager 208 diverts the portion of the fluid stream into secondary conduit 222. Disposed within secondary conduit 222 is a flow disrupter 209. Flow disrupter 209 is configured to impart disturbances to the flow of the portion of the fluid stream within flow conduit 222. Such disturbances include, without limitation, vortices, eddies, pressure fluctuations, and velocity fluctuations. Examples of flow disrupter 209 include, without limitation, a blunt flow disrupter, a planar flow disrupter, a rectangular flow disrupter, and combinations thereof. In certain embodiments, flow disrupter 209 is an actively controlled device. In such embodiments, flow disrupter 209 is coupled to one or more actuators for modifying, without limitation, one or more of the position, shape, and orientation of flow disrupter 209.

Metering system 200 further includes a flow sensor 210 configured to be coupled to flow conduit 222 and to measure a flow characteristic of the portion of the fluid stream within secondary conduit 222. Examples of flow sensor 210 include, without limitation, a calorimetric flow sensor, a hot wire anemometer, a mass flow rate sensor, a volumetric flow rate sensor, a pressure sensor, a temperature sensor, or combinations thereof. For purposes of metering system 200, flow sensor 210 is described as a combination of a mass flow rate sensor and a volumetric flow rate sensor.

Components of metering system 200, including primary conduit 205, secondary flow conduit 222, and sensor 210 (and subcomponents thereof), are generally related by one or more geometrical relationships. Such geometrical relationships include, without limitation, absolute dimensions of the components, relative dimensions of the components with respect to other components, absolute positioning of the components, and relative positioning of the components with respect to other components. More specific examples of such geometrical relationships include, without limitation, respective dimensions of primary conduit 205, secondary conduit 222, and flow disruptor 209; positioning of flow disruptor 209 within secondary conduit 222 relative to sensor 210; dimensions of flow disruptor 209 relative to secondary conduit 222; and dimensions of one of secondary conduit 222 and sensor 210 relative to primary conduit 205. In certain embodiments, dimensions and position of components of metering system 200 are selected to impart specific changes in the fluid stream. For example, in certain embodiments, sensor 210 is dimensioned and positioned relative to secondary conduit 205 to establish a phase difference between a first pressure of the portion of the fluid stream at a first input (not shown) of sensor 210 and a second pressure of the portion of the fluid stream at a second input (not shown) of sensor 210. Furthermore, a value of this phase difference may be selected such that the phase difference results in an increase in a signal-to-noise ratio of an electrical signal generated by sensor 210. By way of example, the phase difference may be selected such that the pressure at the first input of sensor 210 and the pressure at second input of sensor 210 are substantially out-of-phase relative to one another. Such a phase difference facilitates suppressing common mode noise effects in the electrical signal generated by sensor 210.

During operation, flow disruptor 209 disturbs the portion of the fluid stream within secondary conduit 222 and sensor 210 measures at least one flow characteristic of the portion of the fluid stream. Secondary conduit 222 and flow disruptor 209 are dimensioned and arranged such that when the flow rate of the portion of the fluid stream flowing through flow conduit 222 is low, the portion of the fluid stream in the secondary conduit 222 is substantially laminar. For purposes of this disclosure, the term "first flow regime" is used to refer to such flow conditions. Secondary conduit 222 and flow disruptor 209 are further dimensioned and arranged such that when the flow rate of the portion of the fluid stream flowing through flow conduit 222 is substantially high, at least some of the portion of fluid within flow conduit 222 is turbulent due to disturbances induced in the portion of the fluid stream by flow disruptor 209. For purposes of this disclosure, the term "second flow regime" is used to refer to such flow conditions. When in the second flow regime, the temporal characteristics of the vortices, such as the frequency of the vortices, is proportional to the volumetric flow rate of the portion of the fluid stream flowing through flow conduit 222.

Sensor 210 generally includes one or more sensing elements, such as sensing element 211, configured to generate an electrical signal in response to a flow characteristic of the portion of the fluid stream in secondary conduit 222. Examples of sensing element 211 include, without limitation, flow sensing elements, thermopiles, temperature sensing elements, and pressure sensing elements. Any of flow sensing elements, thermopiles, temperature sensing elements, and pressure sensing elements may include one or more micro-electromechanical sensing (MEMS) elements. Sensing element 211 of flow sensor 210 is configured to generate an electrical signal in response to a flow characteristic of the portion of the fluid stream flowing in secondary conduit 222. The electrical signal may correspond to one of a voltage (V) signal (such as a 1-5V signal) or a current (I) signal (such as a 4-20 mA signal) generated by sensing element 211, however, for simplicity, this disclosure generally refers to the electrical signal as a voltage signal.

During operation, the characteristics of the electrical signal depend, at least in part on the flow regime of the portion of the fluid stream within secondary conduit 222. For example, in embodiments in which sensing element 211 measures pressure within secondary conduit 222, the generated electrical signal will be relatively steady when the portion of the fluid stream is in the first flow regime and will exhibit fluctuations caused by vortices and similar disturbances when the portion of the fluid stream is in the second flow regime. More generally, in the first flow regime where few or no vortices are formed, sensing element 211 generates an electrical signal having a voltage magnitude ($V_{amp}$) that is proportional to or otherwise related to the flow characteristic measured by sensing element 211. In contrast, in the second flow regime where vortices are formed, sensing element 211 generates a voltage signal having a voltage frequency ($V_f$) that is proportional to or otherwise related to the flow characteristic measured by sensing element 211.

Figure 3:
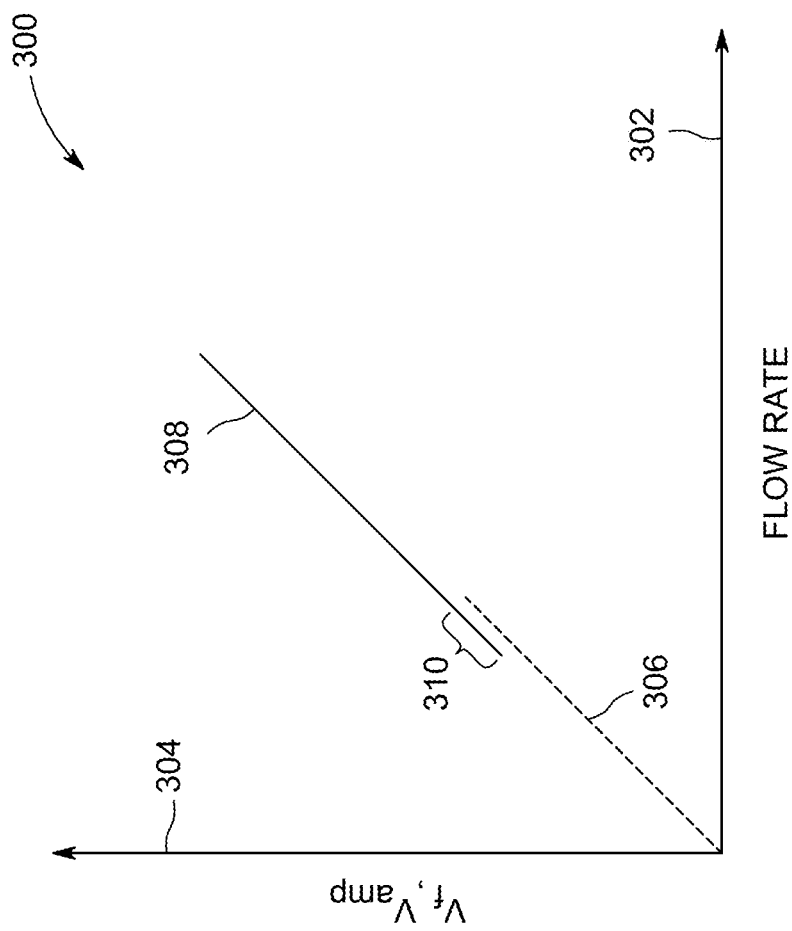
FIG. 3 is a graphical view of a response of a sensor of the metering system of FIG. 2.

FIG. 3 is a graphical view of a response of sensor 210 of metering system 200 (shown in FIG. 2). X-axis 302 of graphical illustration 300 represents a flow rate and, more specifically, a flow rate of a portion of the fluid stream flowing through secondary conduit 222 (shown in FIG. 2), where the flow rate values are unitless. Y-axis 304 represents a magnitude ($V_{amp}$) and a frequency ($V_f$) of a voltage signal generated by sensing element 211 of flow sensor 210, where the voltage values are unitless. As depicted in graphical illustration 300, a first flow regime is represented by a first curve 306 and a second flow regime is represented by a second curve 308. It may be noted that in FIG. 3, first curve 306 and second curve 308 are illustrated as straight lines for purposes of simplicity and should not be interpreted as an indication of a linear relationship between flow rate 302 and sensor response 304.

Reference numeral 310 represents a flow regime, hereinafter referred to as a third flow regime, where first flow regime 306 and second flow regime 308 overlap. As depicted in FIG. 3, third flow regime 310 is located near an upper end of first flow regime 306 and a lower end of second flow regime 308. Accordingly, when flowing in the third flow regime, the portion of the fluid stream within secondary conduit 222 and the resulting electrical signal generated by sensing element 211 exhibits both amplitude and temporal characteristics. In certain embodiments, third flow regime 310 is utilized to facilitate calibration of metering system 200 (shown in FIG. 2). For example, in certain embodiments processor 212 (shown in FIG. 2) performs two calculations of the flow rate of the portion of the fluid stream within conduit 222, the first calculation based on the amplitude characteristics of the electrical signal and the second calculation based on the frequency characteristics of the electrical signal. To the extent the results of the two calculations differ, processor 212 takes corrective action. Such corrective action includes, without limitation, adjusting coefficients and variables used by processor 212 to calculate flow rates.

Figure 4:
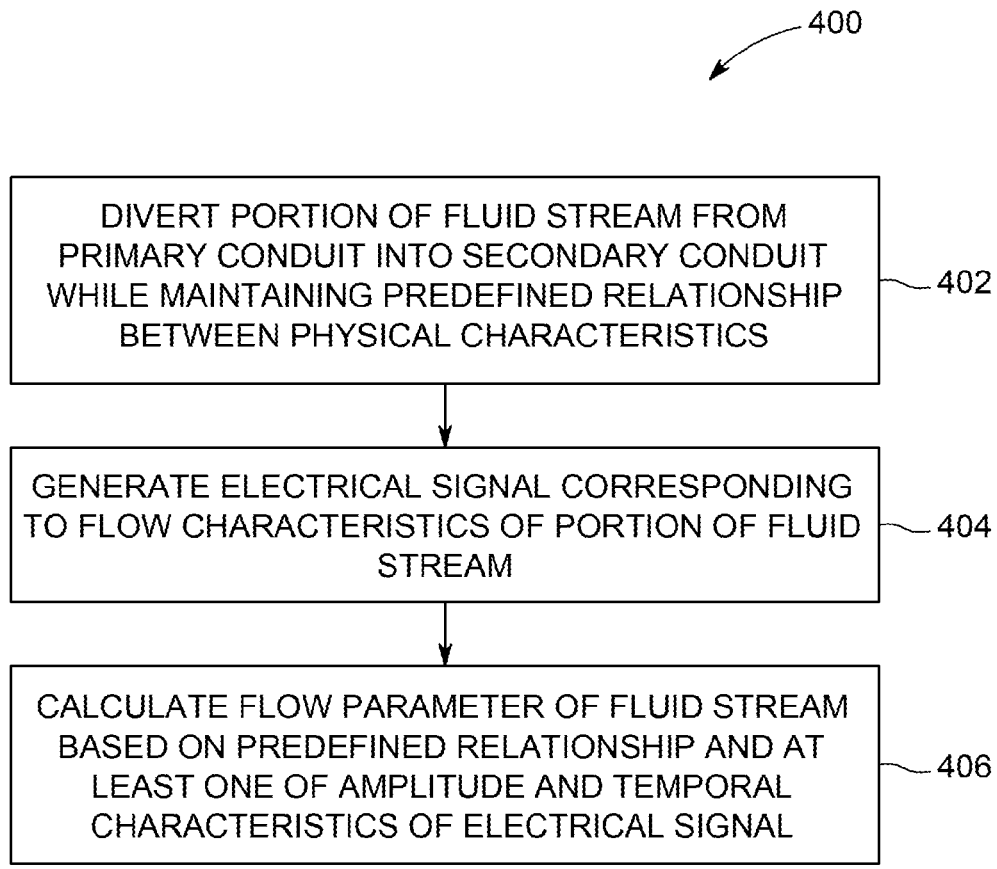
FIG. 4 is a flow chart illustrating an exemplary method for metering a fluid stream.

FIG. 4 is a flow chart illustrating an exemplary method 400 for metering a fluid stream. At step 402, a portion of a fluid stream flowing within a primary conduit is diverted into a secondary conduit in fluid communication with the primary conduit. More specifically, the portion of the fluid stream is diverted into the secondary conduit such that a predetermined relationship between physical characteristics of the fluid stream within the primary conduit and the portion of the fluid stream is maintained. At step 404, a sensor generates an electrical signal corresponding to a flow characteristic of the portion of the fluid stream. At step 406, a flow parameter of the fluid stream within the primary conduit is calculated. The flow parameter is calculated, at least in part, based on the predetermined relationship between physical characteristics and at least one of an amplitude characteristic and a temporal characteristic of the electrical signal. More specifically, the flow parameter is calculated based on the amplitude characteristic if the portion of the fluid stream is in a first flow regime and on the temporal characteristic if the portion of the fluid stream is in a second flow regime. In certain embodiments, the first flow regime corresponds to a substantially laminar flow and the second flow regime corresponds to a substantially turbulent flow.

Figure 5:
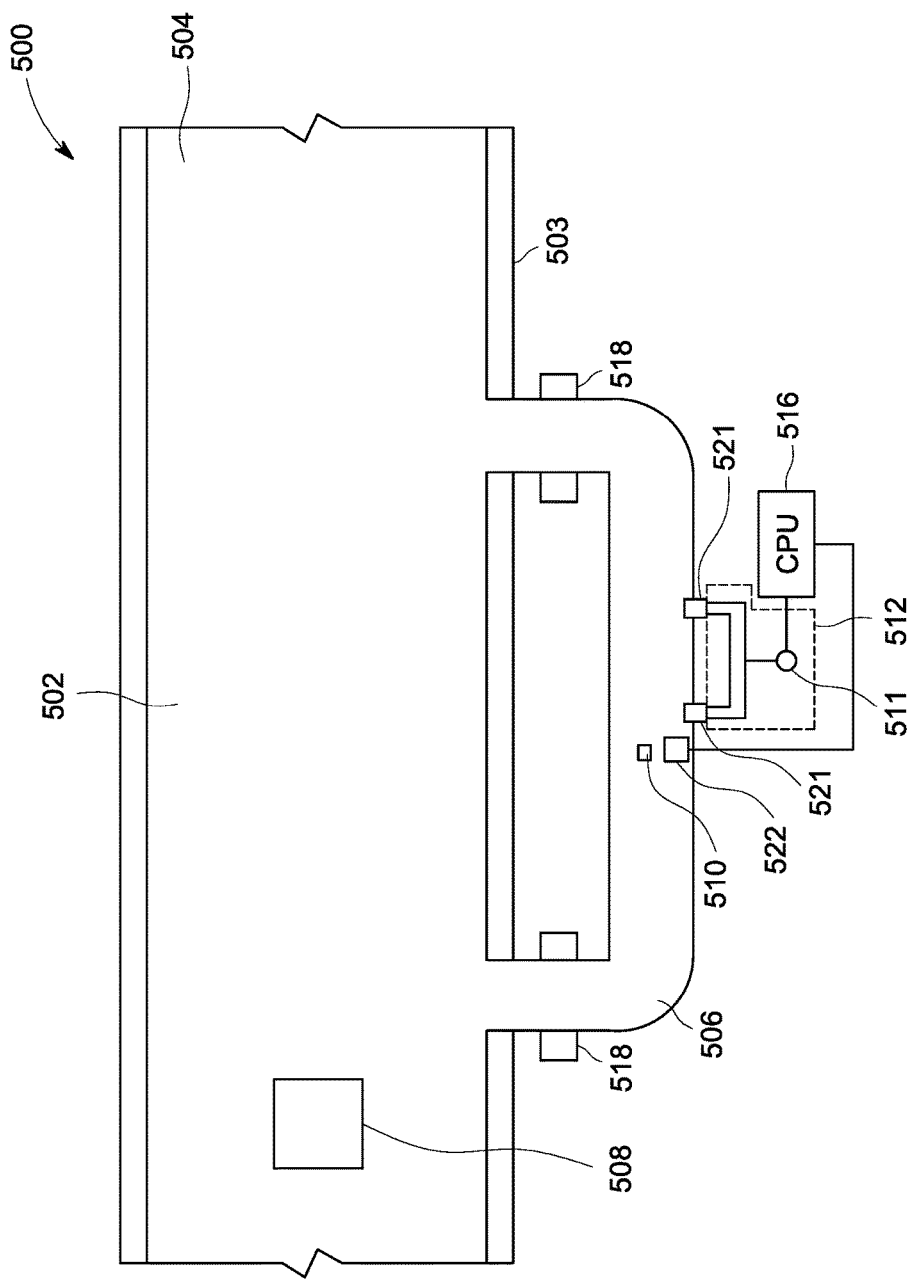
FIG. 5 is a schematic view of another alternative metering system for metering a fluid stream.

FIG. 5 is a schematic view of another alternative metering system 500 for metering a fluid stream. Metering system 500 includes a primary conduit 502 defining a fluid passage 504 extending therethrough. Metering system 500 further includes a secondary conduit 506 in fluid communication with primary conduit 502. During operation, a stream of fluid passes through primary conduit and at least a portion of the fluid stream enters secondary conduit 506.

Flow manager 508 is disposed within primary conduit 502. As described above in the context of flow managers 108 and 208 (shown in FIG. 1 and FIG. 2, respectively) in more detail, flow manager 508 is configured to maintain a predefined relationship between physical characteristics of the fluid stream within primary conduit 502 and the portion of the fluid stream diverted into secondary conduit 506. In metering system 500, flow manager 508 is shown as an obstruction disposed within primary conduit 502. In alternate embodiments, flow manager 508 includes one or more structures or devices, each of which may be passive or actively controlled by a processor, such as processor 516.

A flow disruptor 510 is disposed within secondary conduit 506. Flow disruptor 510 induces disturbances in the portion of the fluid stream within secondary conduit 506. At relatively low flow rates corresponding to a first flow regime, flow disruptor 510 induces little or no disturbances in the portion of the fluid stream such that the portion of the fluid stream is substantially laminar. At relatively high flow rates corresponding to a second flow regime, flow disruptor 510 induces disturbances in the portion of the fluid stream such that the portion of the fluid stream is substantially turbulent. Flow disruptor 510 is shown as an obstruction disposed within fluid passage 504. In other embodiments, flow disruptor 510 may be another structure disposed within secondary conduit 506 including, without limitation, one of an expansion or constriction of secondary conduit 506, a flow straightener, a tube, a baffle, and a fin.

Metering system 500 includes at least one sensor 512 that further includes at least one sensing element 511 configured to generate an electrical signal in response to a flow characteristic of the portion of the fluid stream within secondary conduit 506. Processor 516 is communicatively coupled to sensor 512 and receives electrical signals generated by sensor 512. Processor 516 then determines a flow parameter of the fluid stream within primary conduit 502 based on measurements of the portion of the fluid stream within secondary conduit 506. For example, in certain embodiments, processor 516 determines a flow rate through primary conduit 502 based on a flow rate measured within secondary conduit 506. Processor 516 determines the flow parameter based, at least in part, on the predetermined relationship maintained by flow manager 508 and at least one of an amplitude characteristic and a temporal characteristic of the electrical signal generated by sensor 512. More specifically, when the portion of the fluid within secondary conduit 506 is in the first flow regime, processor 516 determines the flow parameter based on the amplitude characteristic of the electrical signal and when the portion of the fluid stream is in the second flow regime, processor 516 determines the flow parameter based on the temporal characteristic of the electrical signal. In metering system 500, secondary conduit 506 and sensor assembly 512 are detachably coupled to housing 503. More specifically, secondary conduit 506 is coupled to housing 503 by flanges 518 and sensor 512 is coupled to secondary conduit 506 through one or more threaded taps 521. In other embodiments, other suitable couplings may be used in place of one or both of flanges 518 and threaded taps 521 including, without limitation, compression fittings, welded connections, tapered thread connections, and parallel thread connections.

Metering system 500 further includes a regime optimizer 522 communicatively coupled to processor 516. Regime optimizer 522 is a secondary sensor configured to generate an electrical signal, referred to herein as a diagnostic electrical signal, in response to the flow characteristic of the portion of the fluid stream within secondary conduit 506. In certain embodiments, regime optimizer 522 is a low power sensor as compared to sensor 512 and is used primarily to facilitate diagnostic or control functions of metering system 500. For example, in certain embodiments, regime optimizer 522 performs a preliminary sampling of the flow characteristic. In response to the preliminary sampling, processor 516 performs various functions including, without limitation, activating sensor 512, changing a mode of operation of sensor 512 after determining the portion of the fluid stream is in the first or the second flow, determining whether sensor 512 is operational, identifying changes in flow characteristics of the portion of the fluid stream, determining whether the portion of the fluid stream is flowing at within predetermined flow rate ranges, and verifying one or more calibration constants of sensor 512 with respect to at least one of the first flow regime and the second flow regime. In metering system 500, regime optimizer 522 is shown as a separate secondary sensor. In other embodiments, sensor 512 includes or is otherwise configured to operate as regime optimizer 522. For example, in certain embodiments, regime optimizer 522 corresponds to a specific mode of operation of sensor 512.

Figure 6:
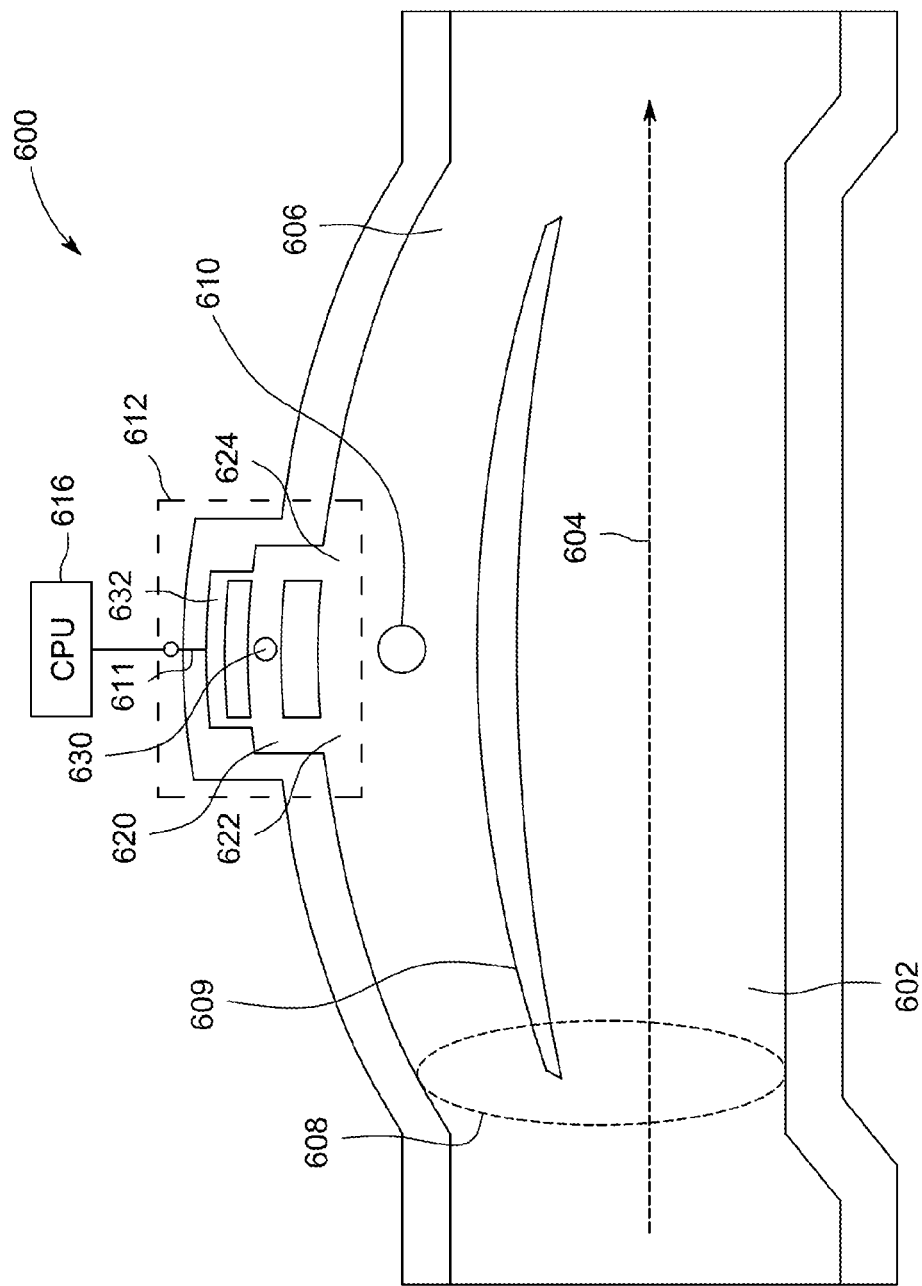
FIG. 6 is a schematic view of yet another alternative metering system for metering a fluid stream.

FIG. 6 is a schematic view of yet another alternative metering system 600 for metering a fluid stream. Metering system 600 includes a primary conduit 602 defining a fluid passage 604 extending therethrough. A secondary conduit 606 is in fluid communication with fluid passage 604. More specifically, secondary conduit 606 is integrally formed with primary conduit 602. A flow manager 608 is included as a combination of a narrowing of primary conduit 602 and flow disruptor 609, and more particularly a fin structure, configured to divide the fluid stream between primary conduit 602 and secondary conduit 606 according to a predetermined ratio based on the geometry of primary conduit 602 and secondary conduit 606. A flow disruptor 610 is disposed in secondary conduit 606 to induce disturbances in the portion of the fluid stream diverted into secondary conduit 606.

A sensor 612 is coupled to secondary conduit 606 and configured to measure a flow characteristic of the portion of the fluid stream. Sensor 612 includes a primary bypass 620 in fluid communication with secondary conduit 606. More specifically, primary bypass 620 includes a bypass inlet 622 upstream of flow disruptor 610 and a bypass outlet 624 downstream of flow disruptor 610. Accordingly a subportion of the portion of the fluid stream entering into fluid conduit enters primary bypass 620. Primary bypass 620 further includes a bypass disruptor 630 that, similar to flow disruptor 609, is configured to induce a disturbance in the subportion of the fluid stream. Sensor 612 further includes a secondary bypass 632 in fluid communication with primary bypass 620 and having a sensing element 611 disposed therein. During operation, sensing element 611 generates an electrical signal in response to a flow characteristic of the subportion of the fluid stream. Processor 616 then calculates a flow parameter of the fluid stream within housing 602 based on a geometrical relationship between one or more components of sensor 612 (e.g., primary bypass 620, secondary bypass 632, bypass disruptor 630) and secondary conduit 606 and fluid passage 604 and one of an amplitude and temporal characteristic of the generated electrical signal.

Figure 7:
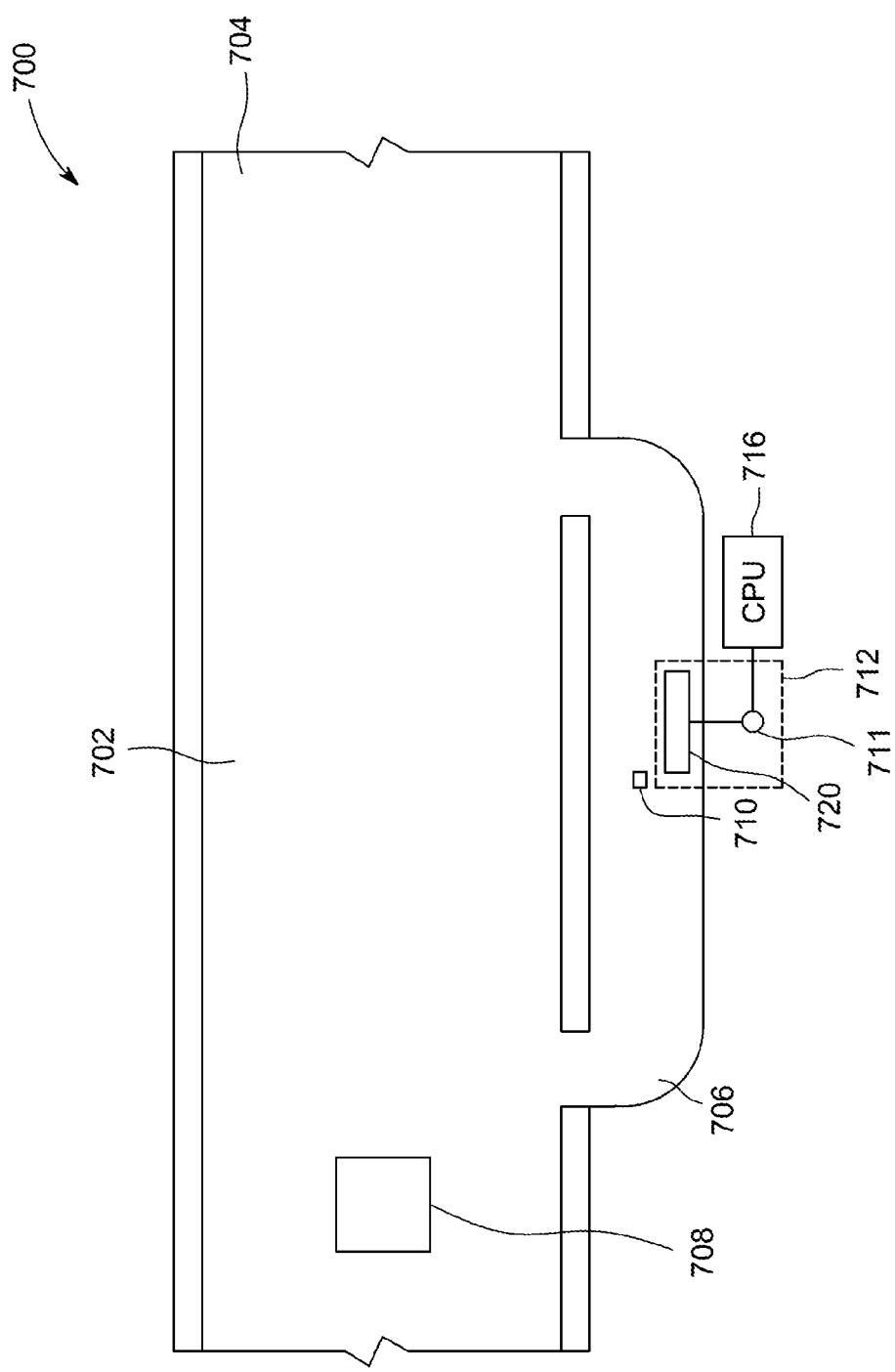
FIG. 7 is a schematic view of another alternative metering system for metering a fluid stream.

FIG. 7 is a schematic view of another alternative metering system 700 for metering a fluid stream. Metering system 700 includes a primary conduit 702 defining a fluid passage 704 extending therethrough. A flow manager 708 is configured to maintain a predefined relationship between physical characteristics of the fluid stream within primary conduit 702 and the portion of the fluid stream diverted into secondary conduit 706. Metering system 700 further includes a secondary conduit 706 in fluid communication with primary conduit 702 and configured to receive a portion of the fluid stream as it passes through primary conduit 702. A sensor 712 measures a flow characteristic of the portion of the fluid stream within secondary conduit 706. In metering system 700, sensor 712 includes a tube 720 disposed in secondary conduit 706 and a sensing element 711 configured to measure a flow characteristic of the portion of the fluid stream as it passes through tube 720. Sensor 712 is communicatively coupled to a processor 716 that is further configured to calculate a flow parameter of the fluid stream within primary conduit 702.

A flow disruptor 710 is disposed within secondary conduit 706. Flow disruptor 710 induces disturbances in the portion of the fluid stream within secondary conduit 706. At relatively low flow rates corresponding to a first flow regime, flow disruptor 710 induces little or no disturbances in the portion of the fluid stream such that the portion of the fluid stream is substantially laminar. At relatively high flow rates corresponding to a second flow regime, flow disruptor 710 induces disturbances in the portion of the fluid stream such that the portion of the fluid stream is substantially turbulent. Flow disruptor 710 is shown as an obstruction disposed within fluid passage 704. In other embodiments, flow disruptor 710 may be another structure disposed within secondary conduit 706 including, without limitation, one of an expansion or constriction of secondary conduit 706, a flow straightener, a tube, a baffle, and a fin.

Figure 8:
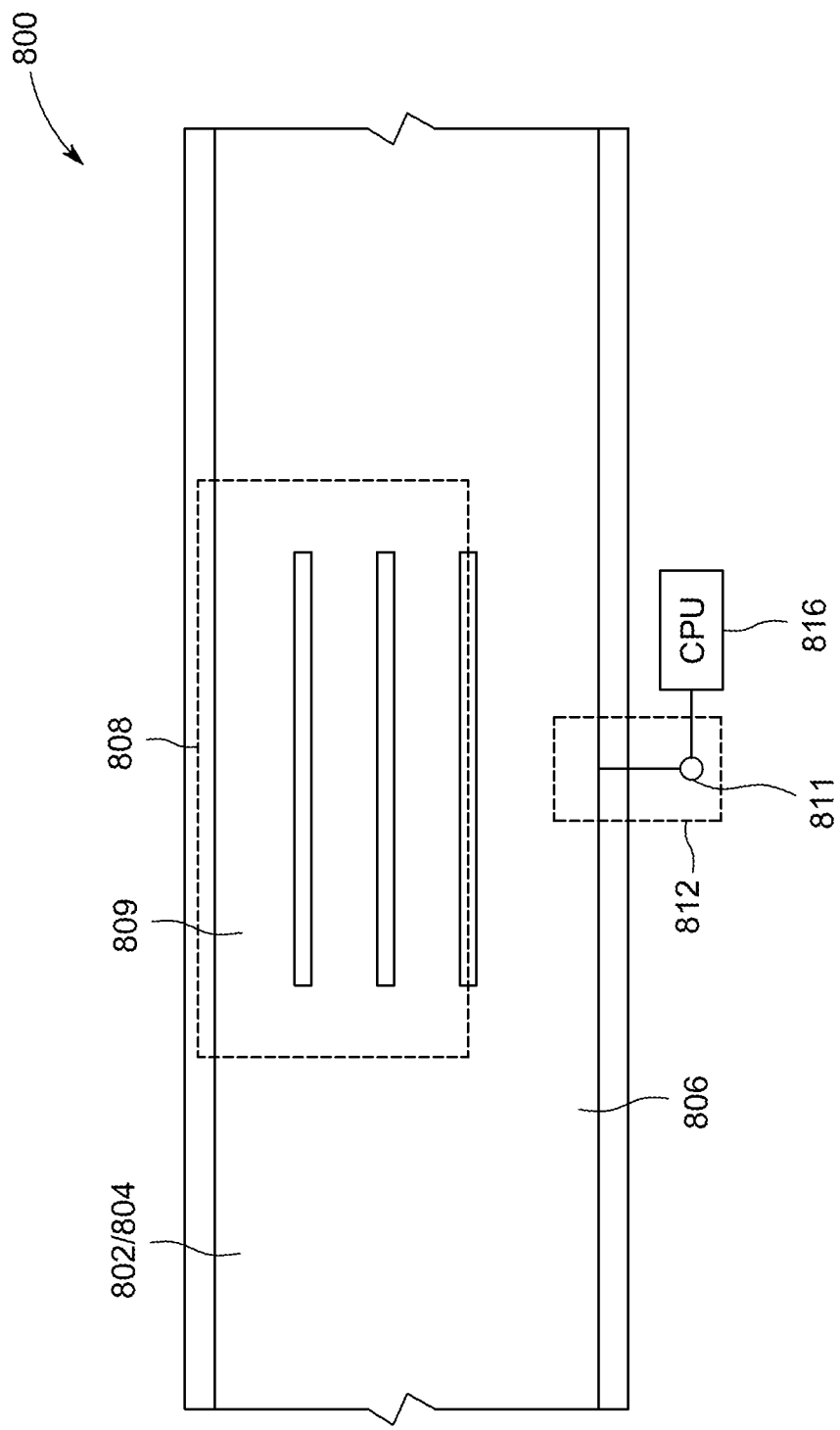
FIG. 8 is a schematic view of yet another alternative metering system for metering a fluid stream.

FIG. 8 is a schematic view of yet another alternative metering system 800 for metering a fluid stream. Metering system 800 includes a primary conduit 802 defining a fluid passage 804 extending therethrough. Metering system 800 further includes a secondary conduit 806 in fluid communication with primary conduit 802 and configured to receive a portion of the fluid stream as it passes through primary conduit 802. A flow manager 808 maintains a predetermined relationship between physical characteristics of the fluid stream within primary conduit 802 and the portion of the fluid stream within secondary conduit 806. More specifically, flow manager 808 includes a plurality of flow passages (such as flow passage 809) defined within primary conduit 802. Secondary conduit 806 is generally identical to the flow passages such that as the fluid stream passes through primary conduit 802, the fluid stream is equally divided between flow manager 808 and secondary conduit 806. A sensor 812 is disposed within secondary conduit 806 and includes a sensing element 811 configured to measure a flow characteristic of the portion of the fluid stream as it passes through secondary conduit 806. Sensor 812 is communicatively coupled to a processor 816 that is further configured to calculate a flow parameter of the fluid stream within primary conduit 802. More specifically, processor 816 is configured to calculate a flow parameter of the fluid stream within primary conduit 802.

The above-described metering system provides an efficient and accurate means for metering fluids streams and, in particular, gas streams. Specifically, the described metering system determines flow parameters of a fluid stream within a primary conduit across a wide range of operational conditions via a sensor disposed in a secondary conduit coupled to the primary conduit. A processor coupled to the sensor correlates amplitude and/or temporal characteristics of electrical signals generated by the sensor and geometrical relationships between the primary conduit and one or more of the secondary conduit and the sensor.

An exemplary technical effect of the methods and apparatus described herein includes at least one of: (a) improving metering accuracy over a wide range of flow conditions; (b) minimizing effects on metering accuracy caused by fluctuations in fluid stream properties; and (c) enabling the use of a standardized metering assemblies over a wide range of primary conduit sizes, ratings, and flow rates.

Exemplary embodiments of the metering system are described above in detail. The metering system, and methods of operating such units and devices, are not limited to the specific embodiments described herein, but rather, components of systems and/or steps of the methods may be utilized independently and separately from other components and/or steps described herein. For example, the methods may also be used in combination with other systems for fluid metering, and are not limited to practice with only the systems and methods described herein. Rather, the exemplary embodiment may be implemented and utilized in connection with many other fluid metering applications that require accurate metering over a wide range of operational conditions.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to describe the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for metering a fluid stream, said system comprising:
a primary conduit;
a secondary conduit in fluid communication with said primary conduit and configured to receive a portion of a fluid stream passing through said primary conduit;
a flow manager disposed in said primary conduit and configured to maintain a predetermined relationship between at least one first physical characteristic of the fluid stream and at least one second physical characteristic of the portion of the fluid stream;
a sensor configured to generate an electrical signal in response to a flow characteristic of the portion of the fluid stream; and
a processor communicatively coupled to said sensor and configured to determine a flow parameter of the fluid stream based, at least in part, on the predetermined relationship between the at least one first physical characteristic of the fluid stream and the at least one second physical characteristic of the portion of the fluid stream, and at least one of an amplitude characteristic of the electrical signal and a temporal characteristic of the electrical signal, wherein said processor determines the flow parameter of the fluid stream based on the amplitude characteristic when the portion of the fluid stream is in a first flow regime and based on the temporal characteristic when the portion of the fluid stream is in a second flow regime.

2. The system in accordance with claim 1, wherein the first flow regime is substantially laminar and the second flow regime is substantially turbulent.

3. The system in accordance with claim 1, wherein said processor further determines the flow parameter of the fluid stream based on a geometrical relationship between said primary conduit and at least one of said secondary conduit and said sensor.

4. The system in accordance with claim 1 further comprising a flow disrupter disposed in said secondary conduit and configured to induce disturbances in the portion of the fluid stream when the portion of the fluid stream exceeds a predetermined flow rate, wherein the degree of induced disturbances cause the portion of the fluid stream to flow in one of the first flow regime and the second flow regime.

5. The system in accordance with claim 1, wherein the at least one first physical characteristic and the at least one second characteristic are one of separability, pressure, temperature, mass flow rate, volumetric flow rate, and a level of impurities.

6. The system in accordance with claim 1, wherein at least one of said sensor and said secondary conduit are detachably coupled to said primary conduit.

7. The system in accordance with claim 1, wherein said secondary conduit is integral with said primary conduit.

8. The system in accordance with claim 7, wherein said secondary conduit is disposed within said primary conduit.

9. The system in accordance with claim 1, wherein said processor is further configured to calibrate said sensor based on a third flow regime, the third flow regime corresponding to an overlap region of the first flow regime and the second flow regime.

10. The system in accordance with claim 1, further comprising:
a regime optimizer communicatively coupled to said processor, said regime optimizer configured to generate a diagnostic electrical signal in response to the flow characteristic of the portion of the fluid stream, wherein said processor is further configured to perform at least one diagnostic function based, at least in part, on said diagnostic electrical signal.

11. The system in accordance with claim 10, wherein said at least one diagnostic includes one of: activating said sensor, changing said sensor between a first mode of operation corresponding to the first flow regime and a second mode of operation corresponding to the second flow regime, changing said sensor to a third mode of operation corresponding to a third flow regime corresponding to an overlap of the first flow regime and the second flow regime, confirming that said sensor is operational, identifying a change in the flow characteristic of the portion of the fluid stream, determining that the portion of the fluid stream has a flow rate within a predetermined flow rate range, and verifying one or more calibration constants of said sensor.

12. The system in accordance with claim 1, wherein said sensor defines a bypass channel in fluid communication with said secondary conduit, said bypass channel configured to receive a subportion of the fluid stream, wherein the flow characteristic of the portion of the fluid stream is a flow characteristic of the subportion of the fluid stream.

13. A metering assembly for use in a fluid meter, the fluid meter including a primary conduit, the metering assembly comprising:
a secondary conduit configured to be coupled to the primary conduit and configured to receive, when coupled to the primary conduit, a portion of a fluid stream passing through the primary conduit;

a flow manager disposed in said primary conduit and configured to maintain a predetermined relationship between at least one first physical characteristic of the fluid stream and at least one second physical characteristic of the portion of the fluid stream;

a sensor configured to generate an electrical signal in response to a flow characteristic of the portion of the fluid stream; and a processor communicatively coupled to said sensor and configured to determine a flow parameter of the fluid stream based, at least in part, the predetermined relationship between the at least one first physical characteristic of the fluid stream and the at least one second physical characteristic of the portion of the fluid stream, and at least one of an amplitude characteristic of the electrical signal and a temporal characteristic of the electrical signal, wherein said processor determines the flow parameter of the fluid stream based on the amplitude characteristic when the portion of the fluid stream is in a first flow regime and based on the temporal characteristic when the portion of the fluid stream is in a second flow regime.

14. The metering assembly in accordance with claim 13, wherein the first flow regime is substantially laminar and the second flow regime is substantially turbulent.

15. The metering assembly in accordance with claim 13, wherein said processor further determines the flow parameter of the fluid stream based on a geometrical relationship between said primary conduit and at least one of said secondary conduit and said sensor.

16. The metering assembly in accordance with claim 13, further comprising a flow disrupter disposed in said secondary conduit and configured to induce disturbances in the portion of the fluid stream when the portion of the fluid stream exceeds a predetermined flow rate, wherein the degree of induced disturbances cause the portion of the fluid stream to flow in one of the first flow regime and the second flow regime.

17. The metering assembly in accordance with claim 13, wherein the at least one first physical characteristic and the at least one second characteristic are one of separability, pressure, temperature, mass flow rate, volumetric flow rate, and a level of impurities.

18. The metering assembly in accordance with claim 13, wherein said processor is further configured to calibrate said sensor based on a third flow regime, the third flow regime corresponding to an overlap region of the first flow regime and the second flow regime.

19. The metering assembly in accordance with claim 13, further comprising:

a regime optimizer communicatively coupled to said processor, said regime optimizer configured to generate a diagnostic electrical signal in response to the flow characteristic of the portion of the fluid stream, wherein said processor is further configured to perform at least one diagnostic function based, at least in part, on said diagnostic electrical signal.

20. The metering assembly in accordance with claim 19, wherein said at least one diagnostic includes one of: activating said sensor, changing said sensor between a first mode of operation corresponding to the first flow regime and a second mode of operation corresponding to the second flow regime, changing said sensor to a third mode of operation corresponding to a third flow regime corresponding to an overlap of the first flow regime and the second flow regime, confirming that said sensor is operational, identifying a change in the flow characteristic of the portion of the fluid stream, determining that the portion of the fluid stream has a flow rate within a predetermined flow rate range, and verifying one or more calibration constants of said sensor.

21. A method for metering a fluid stream within a primary conduit, said method comprising:

diverting a portion of the fluid stream into a secondary conduit, wherein diverting the portion of the fluid stream includes maintaining a predetermined relationship between at least one first physical characteristic of the fluid stream and at least one second physical characteristic of the portion of the fluid stream;

generating, by a sensor, an electrical signal corresponding to a flow characteristic of the portion of the fluid stream; and calculating a flow parameter of the fluid stream based, at least in part, on the predetermined relationship between the at least one first physical characteristic of the fluid stream and the at least one second physical characteristic of the portion of the fluid stream, and at least one of an amplitude characteristic of the electrical signal and a temporal characteristic of the electrical signal, wherein calculating the flow parameter of the fluid stream is based on the amplitude characteristic when the portion of the fluid stream is in a first flow regime and on the temporal characteristic when the portion of the fluid stream is in a second flow regime.

22. The method in accordance with claim 21, wherein the first flow regime is substantially laminar and the second flow regime is substantially turbulent.

23. The method in accordance with claim 21, wherein calculating the flow parameter of the fluid stream is further based on a geometric relationship between the primary conduit and at least one of the secondary conduit and the sensor.

24. The method in accordance with claim 21 further comprising calibrating the sensor based on a third flow regime, the third flow regime corresponding to an overlap region of the first flow regime and the second flow regime.

* * * * *